United States Patent
Alexanderson et al.

(10) Patent No.: US 12,262,453 B2
(45) Date of Patent: Mar. 25, 2025

(54) POWER MODULATION FOR POWERING ONE OR MORE LIGHT SOURCES

(71) Applicant: Stryker Corporation, Kalamazoo, MI (US)

(72) Inventors: James Kenneth Alexanderson, Coppell, TX (US); Robert Lee York, Lantana, TX (US)

(73) Assignee: Stryker Corporation, Portage, MI (US)

( * ) Notice: Subject to any disclaimer, the term of this patent is extended or adjusted under 35 U.S.C. 154(b) by 19 days.

(21) Appl. No.: 18/067,012

(22) Filed: Dec. 15, 2022

(65) Prior Publication Data
US 2023/0199926 A1 Jun. 22, 2023

Related U.S. Application Data

(60) Provisional application No. 63/265,691, filed on Dec. 17, 2021.

(51) Int. Cl.
*H05B 45/10* (2020.01)
*A61B 90/30* (2016.01)

(52) U.S. Cl.
CPC .............. *H05B 45/10* (2020.01); *A61B 90/30* (2016.02)

(58) Field of Classification Search
CPC .... H05B 45/10; H05B 45/335; H05B 45/325; H05B 45/305; H05B 45/32; A61B 90/30
See application file for complete search history.

(56) References Cited

U.S. PATENT DOCUMENTS

| | | | |
|---|---|---|---|
| 7,852,017 B1 | 12/2010 | Melanson | |
| 9,510,414 B2 * | 11/2016 | Kim | H05B 45/31 |
| 10,368,410 B2 | 7/2019 | Qi | |
| 2009/0108204 A1 * | 4/2009 | Ohashi | H04J 13/102 |
| | | | 250/339.06 |
| 2015/0373796 A1 * | 12/2015 | Bahrehmand | H05B 45/325 |
| | | | 315/129 |
| 2021/0227658 A1 * | 7/2021 | Peng | H05B 45/10 |

FOREIGN PATENT DOCUMENTS

| | | |
|---|---|---|
| CN | 201805593 U | 4/2011 |
| CN | 112951149 A | 6/2021 |

* cited by examiner

*Primary Examiner* — Minh D A
(74) *Attorney, Agent, or Firm* — Morrison & Foerster LLP

(57) ABSTRACT

Disclosed herein are systems and methods for powering light sources to reduce optical and/or electrical interference between the light sources and optical components in the same environment. The light sources may be powered using power modulation signals, whose frequency may be varied across modulation periods. Optionally, the frequency may be varied randomly or pseudo randomly. The systems and methods may additionally or alternatively introduce phase modulation into the control signals for driving channels of light sources. A phase difference in the control signals to at least two channels can reduce or avoid simultaneous or synchronous driving of the channels. The systems and methods described herein can vary one or more properties (e.g., frequency, phase shift, delay, duty cycle, power, etc.) of the power modulation signals.

29 Claims, 10 Drawing Sheets

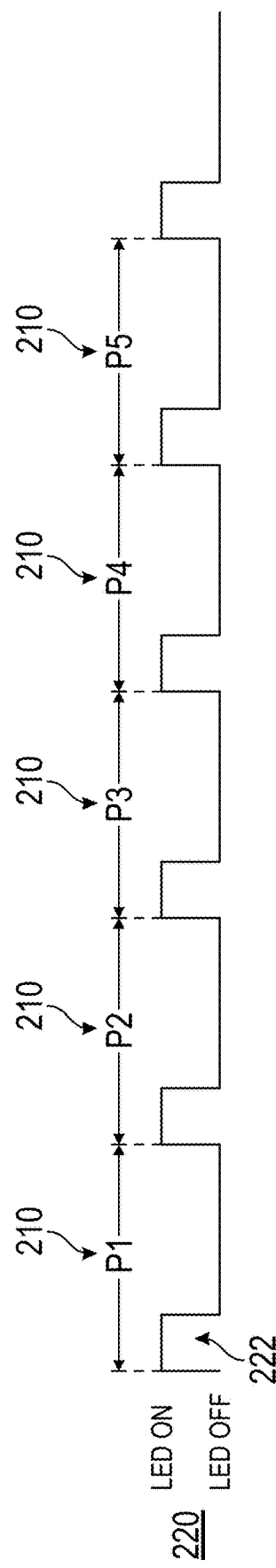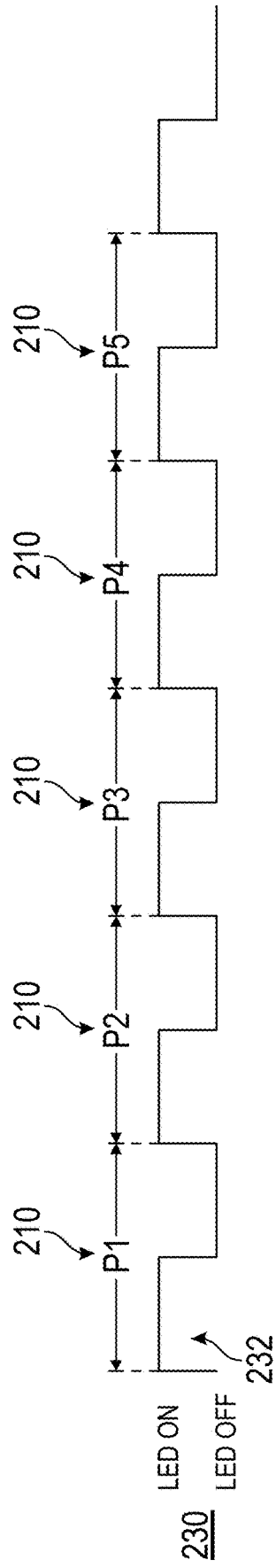

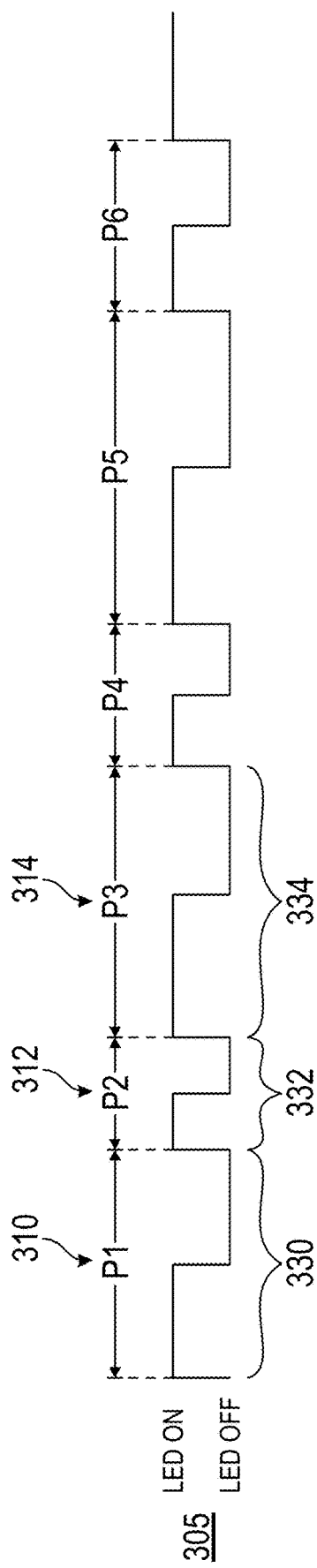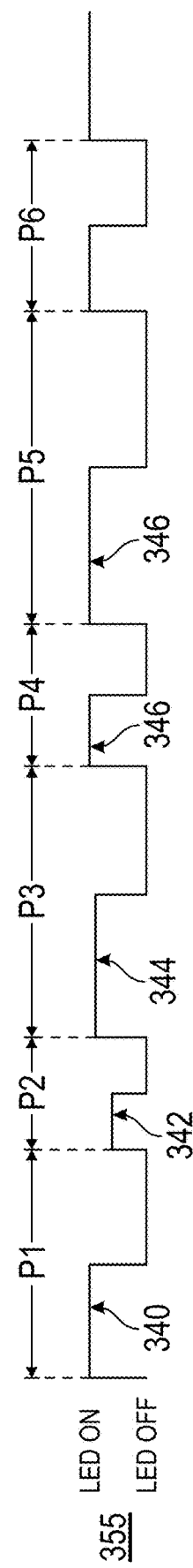
FIG. 3A
FIG. 3B

POWER MODULATION FOR POWERING ONE OR MORE LIGHT SOURCES

CROSS-REFERENCE TO RELATED APPLICATIONS

This application claims the benefit of U.S. Provisional Application No. 63/265,691, filed Dec. 17, 2021, the entire contents of which are hereby incorporated by reference herein.

FIELD

The present invention relates to lighting sources, and in particular, to powering one or more light sources using power modulation.

BACKGROUND

Light sources (e.g., surgical lights) are used for many applications, such as in operating rooms to provide relatively high intensity light to a target surgical area for illuminating the target surgical area during surgery. For example, the surgical light can be positioned within an operating room and can provide increased light to a specific area of a person being operated on within the operating room. The amount of increased light may be based on the intensity of light emanating from the surgical lights.

The current standard for a modern light source, including surgical lights, is to use light emitting diodes (LEDs). One method for controlling the LED intensity is to use analog control. Analog control involves applying a linear signal, where a higher current results in increased intensity, and a lower current results in decreased intensity. However, it may not be suitable to use analog control when the light sources are operated at low intensity levels due to, e.g., color shifting and heating issues.

Another method for controlling the intensity of the light source(s) is to use power modulation, such as pulse width modulation (PWM). PWM involves pulsing the light source(s) at a fixed frequency (e.g., 1500 Hz). The frequency is too fast for the human eye to notice the pulsing. The intensity may be controlled based on the proportion of ON time compared to OFF time of the pulses. A longer ON time results in increased intensity, and a shorter ON time results in decreased intensity.

The light source(s) may be located in an environment comprising other optical components (or systems). One exemplary environment may be an operating room equipped with surgical lights in addition to other optical components such as video cameras. These other optical components may be operating at the same time and may be susceptible to optical and/or electrical interference. For example, the surgical lights may cause interference on a camera's video if the modulation frequency (or harmonic thereof) of the signals driving the light source(s) is similar to the shutter speed of the video camera. This interference may be reduced by changing the modulation frequency such that it does not correspond to the shutter speed of the video camera. However, the changed modulation frequency may interfere with other optical components/systems in the operating room. As a result, the fixed frequency power modulated light source(s) may optically and/or electrically interfere with other optical components, preventing the optical component(s) from operating properly.

SUMMARY

According to various aspects, systems and methods include reducing or avoiding interference when powering one or more light sources. The interference may be any type of interference, such as optical and electrical. The one or more light sources may be powered using power modulation signals having a frequency that varies. Optionally, the one or more light sources may be powered using the power modulation signals when an input to or an output from the light sources is less than a pre-determined level, but then switched to analog control when greater than or equal to the pre-determined level. Additionally or alternatively, channels of light sources may be powered using phase modulation across the channels.

According to some examples, a method of powering one or more light sources comprises: providing one or more input frequencies to a spread spectrum oscillator, wherein the spread spectrum oscillator generates an input signal based on the one or more input frequencies; generating one or more power modulation signals based on the input signal, wherein the one or more power modulation signals have a frequency that varies across modulation periods; providing the one or more power modulation signals to one or more power circuits; and driving the one or more light sources using one or more control signals generated by the one or more power circuits, wherein the one or more control signals are based on at least the one or more power modulation signals.

In any of these examples, the frequency of the one or more power modulation signals for a first modulation period is different from the frequency of the one or more power modulation signals for a second modulation period, wherein the first modulation period and the second modulation period are consecutive periods.

In any of these examples, the frequency of the one or more power modulation signals varies randomly or pseudo randomly.

In any of these examples, a duty cycle of the one or more power modulation signals is the same across the modulation periods.

In any of these examples, a duty cycle of the one or more power modulation signals varies across the modulation periods.

In any of these examples, the driving the one or more light sources comprises driving the same power during ON times of at least two of the modulation periods.

In any of these examples, the driving the one or more light sources comprises driving different powers during ON times of at least two of the modulation periods.

In any of these examples, the method further comprises: adjusting an intensity of light emanating from the one or more light sources, the adjusting comprising changing a duty cycle of the one or more power modulation signals without changing the one or more input frequencies.

In any of these examples, the method further comprises: providing one or more linear signals to the one or more power circuits, wherein the one or more control signals are further based on the one or more linear signals.

In any of these examples, when an input to or an output from the one or more light sources is greater than or equal to a pre-determined level, an intensity of light emanating from the one or more light sources is controlled based on the one or more linear signals, and when the input to or the output from the one or more light sources is less than the pre-determined level, the intensity of the light emanating from the one or more light sources is controlled based on the one or more power modulation signals.

According to some examples, a system comprises: one or more light sources; a controller that: provides one or more input frequencies to a spread spectrum oscillator, wherein the spread spectrum oscillator generates an input signal based on the one or more input frequencies; and generates one or more power modulation signals based on the input signal, wherein the one or more power modulation signals have a frequency that varies across modulation periods; and one or more power circuits that receive the one or more power modulation signals and generate one or more control signals to drive the one or more light sources, wherein the one or more control signals are based on at least the one or more power modulation signals.

In any of these examples, the system further comprises: one or more optical components, wherein during at least one modulation period, the one or more optical components operate at a frequency different from the frequency of the one or more power modulation signals.

In any of these examples, the one or more optical components comprise at least one of: a video camera, a pulse oximeter, an optical navigation system, or a location sensor.

In any of these examples, the frequency of the one or more power modulation signals for a first modulation period is different from the frequency of the one or more power modulation signals for a second modulation period, wherein the first modulation period and the second modulation period are consecutive periods.

In any of these examples, the frequency of the one or more power modulation signals varies randomly or pseudo randomly.

In any of these examples, a duty cycle of the one or more power modulation signals is the same across the modulation periods.

In any of these examples, a duty cycle of the one or more power modulation signals varies across the modulation periods.

In any of these examples, the one or more power circuits drive the one or more light sources using the same power during ON times of at least two of the modulation periods.

In any of these examples, the one or more power circuits drive the one or more light sources using different powers during ON times of at least two of the modulation periods.

In any of these examples, the one or more power circuits further receive one or more linear signals, and wherein the one or more control signals are further based on the one or more linear signals.

In any of these examples, when an input to or an output from the one or more light sources is greater than or equal to a pre-determined level, an intensity of light emanating from the one or more light sources is controlled based on the one or more linear signals, and when the input to or the output from the one or more light sources is less than the pre-determined level, the intensity of the light emanating from the one or more light sources is controlled based on the one or more power modulation signals.

According to some examples, a system for powering one or more light sources, the system comprising one or more processors, memory, and one or more programs stored in the memory for execution by the one or more processors and including instructions for: providing one or more input frequencies to a spread spectrum oscillator, wherein the spread spectrum oscillator generates an input signal based on the one or more input frequencies; generating one or more power modulation signals based on the input signal, wherein the one or more power modulation signals have a frequency that varies across modulation periods; providing the one or more power modulation signals to one or more power circuits; and driving the one or more light sources using one or more control signals generated by the one or more power circuits, wherein the one or more control signals are based on at least the one or more power modulation signals.

In any of these examples, the frequency of the one or more power modulation signals for a first modulation period is different from the frequency of the one or more power modulation signals for a second modulation period, wherein the first modulation period and the second modulation period are consecutive periods.

In any of these examples, the frequency of the one or more power modulation signals varies randomly or pseudo randomly.

In any of these examples, a duty cycle of the one or more power modulation signals is the same across the modulation periods.

In any of these examples, a duty cycle of the one or more power modulation signals varies across the modulation periods.

In any of these examples, the driving the one or more light sources comprises driving the same power during ON times of at least two of the modulation periods.

In any of these examples, the driving the one or more light sources comprises driving different powers during ON times of at least two of the modulation periods.

In any of these examples, the one or more programs include further instructions for adjusting an intensity of light emanating from the one or more light sources, the adjusting comprising changing a duty cycle of the one or more power modulation signals without changing the one or more input frequencies.

In any of these examples, the one or more programs include further instructions for providing one or more linear signals to the one or more power circuits, wherein the one or more control signals are further based on the one or more linear signals.

In any of these examples, when an input to or an output from the one or more light sources is greater than or equal to a pre-determined level, an intensity of light emanating from the one or more light sources is controlled based on the one or more linear signals, and when the input to or the output from the one or more light sources is less than the pre-determined level, the intensity of the light emanating from the one or more light sources is controlled based on the one or more power modulation signals.

According to some examples, a method of powering one or more light sources comprises: generating a plurality of power modulation signals based on an input signal, the plurality of power modulation signals comprising at least a first power modulation signal and a second power modulation signal, wherein a phase shift of the first power modulation signal is different from a phase shift of the second power modulation signal during the same modulation period; providing the plurality of power modulation signals to one or more power circuits; and driving the one or more light sources using one or more control signals generated by the one or more power circuits, wherein the one or more control signals are based on at least the plurality of power modulation signals.

In any of these examples, a difference between the phase shift of the first power modulation signal and the phase shift of the second power modulation signal is the same over modulation periods.

In any of these examples, a difference between the phase shift of the first power modulation signal and the phase shift of the second power modulation signal varies over modulation periods.

In any of these examples, the difference between the phase shift of the first power modulation signal and the phase shift of the second power modulation signal varies randomly or pseudo randomly.

In any of these examples, a difference between the phase shift of the first power modulation signal and the phase shift of the second power modulation signal is based on a number of the plurality of power modulation signals.

In any of these examples, the method further comprises: providing one or more input frequencies to an oscillator, wherein the oscillator generates the input signal based on the one or more input frequencies.

In any of these examples, the oscillator is a spread spectrum oscillator.

In any of these examples, a duty cycle of the plurality of power modulation signals is the same across modulation periods.

In any of these examples, a duty cycle of the plurality of power modulation signals varies across modulation periods.

In any of these examples, the driving the one or more light sources comprises driving the same power during ON times of at least two modulation periods.

In any of these examples, the driving the one or more light sources comprises driving different powers during ON times of at least two modulation periods.

In any of these examples, the method further comprises: adjusting an intensity of light emanating from the one or more light sources, the adjusting comprising changing a duty cycle of the plurality of power modulation signals without changing the one or more input frequencies.

In any of these examples, the method further comprises: providing one or more linear signals to the one or more power circuits, wherein the one or more control signals are further based on the one or more linear signals.

In any of these examples, when an input to or an output from the one or more light sources is greater than or equal to a pre-determined level, an intensity of light emanating from the one or more light sources is controlled based on the one or more linear signals, and when the input to or the output from the one or more light sources is less than the pre-determined level, the intensity of the light emanating from the one or more light sources is controlled based on the one or more power modulation signals.

According to some examples, a system comprises: one or more light sources; a controller that generates a plurality of power modulation signals based on an input signal, the plurality of power modulation signals comprising at least a first power modulation signal and a second power modulation signal, wherein a phase shift of the first power modulation signal is different from a phase shift of the second power modulation signal during the same modulation period; and one or more power circuits that receive the plurality of power modulation signals and generate one or more control signals to drive the one or more light sources, wherein the one or more control signals are based on at least the plurality of power modulation signals.

In any of these examples, the system further comprises: one or more optical components, wherein during at least one modulation period, the one or more optical components operate with a phase shift different from a phase shift of at least one of the plurality of power modulation signals.

In any of these examples, the one or more optical components comprise at least one of: a video camera, a pulse oximeter, an optical navigation system, or a location sensor.

In any of these examples, a difference between the phase shift of the first power modulation signal and the phase shift of the second power modulation signal is the same over modulation periods.

In any of these examples, a difference between the phase shift of the first power modulation signal and the phase shift of the second power modulation signal varies over modulation periods.

In any of these examples, the difference between the phase shift of the first power modulation signal and the phase shift of the second power modulation signal varies randomly or pseudo randomly.

In any of these examples, the difference between the phase shift of the first power modulation signal and the phase shift of the second power modulation signal is based on a number of the plurality of power modulation signals.

In any of these examples, the system further comprises: an oscillator that generates the input signal based on one or more input frequencies, wherein the controller provides the one or more input frequencies to the oscillator.

In any of these examples, the oscillator is a spread spectrum oscillator.

In any of these examples, a duty cycle of the plurality of power modulation signals is the same across modulation periods.

In any of these examples, a duty cycle of the plurality of power modulation signals varies across modulation periods.

In any of these examples, the one or more power circuits drive the one or more light sources using the same power during ON times of at least two modulation periods.

In any of these examples, the one or more power circuits drive the one or more light sources using different powers during ON times of at least two modulation periods.

In any of these examples, the one or more power circuits further receives one or more linear signals, and wherein the one or more control signals are further based on the one or more linear signals.

In any of these examples, when an input to or an output from the one or more light sources is greater than or equal to a pre-determined level, an intensity of light emanating from the one or more light sources is controlled based on the one or more linear signals, and when the input to or the output from the one or more light sources is less than the pre-determined level, the intensity of the light emanating from the one or more light sources is controlled based on the one or more power modulation signals.

According to some examples, a system for powering one or more light sources comprises one or more processors, memory, and one or more programs stored in the memory for execution by the one or more processors and including instructions for: generating a plurality of power modulation signals based on an input signal, the plurality of power modulation signals comprising at least a first power modulation signal and a second power modulation signal, wherein a phase shift of the first power modulation signal is different from a phase shift of the second power modulation signal during the same modulation period; providing the plurality of power modulation signals to one or more power circuits; and driving the one or more light sources using one or more control signals generated by the one or more power circuits, wherein the one or more control signals are based on at least the plurality of power modulation signals.

In any of these examples, a difference between the phase shift of the first power modulation signal and the phase shift of the second power modulation signal is the same over modulation periods.

In any of these examples, a difference between the phase shift of the first power modulation signal and the phase shift of the second power modulation signal varies over modulation periods.

In any of these examples, the difference between the phase shift of the first power modulation signal and the phase shift of the second power modulation signal varies randomly or pseudo randomly.

In any of these examples, the difference between the phase shift of the first power modulation signal and the phase shift of the second power modulation signal is based on a number of the plurality of power modulation signals.

In any of these examples, the one or more programs include further instructions for providing one or more input frequencies to an oscillator, wherein the oscillator generates the input signal based on the one or more input frequencies;

In any of these examples, the oscillator is a spread spectrum oscillator.

In any of these examples, a duty cycle of the plurality of power modulation signals is the same across modulation periods.

In any of these examples, a duty cycle of the plurality of power modulation signals varies across modulation periods.

In any of these examples, the driving the one or more light sources comprises driving the same power during ON times of at least two modulation periods.

In any of these examples, the driving the one or more light sources comprises driving different powers during ON times of at least two modulation periods.

In any of these examples, the one or more programs include further instructions for adjusting an intensity of light emanating from the one or more light sources, the adjusting comprising changing a duty cycle of the plurality of power modulation signals without changing the one or more input frequencies.

In any of these examples, the driving the one or more light sources comprises providing one or more linear signals to the one or more power circuits, wherein the one or more control signals are further based on the one or more linear signals.

In any of these examples, when an input to or an output from the one or more light sources is greater than or equal to a pre-determined level, an intensity of light emanating from the one or more light sources is controlled based on the one or more linear signals, and when the input to or the output from the one or more light sources is less than the pre-determined level, the intensity of the light emanating from the one or more light sources is controlled based on the one or more power modulation signals.

According to some examples, a method of powering one or more light sources comprises: providing one or more input frequencies to a plurality of oscillators, wherein the plurality of oscillators generates a plurality of input signals based on the one or more input frequencies; generating a plurality of power modulation signals based on the plurality of input signals, the plurality of power modulation signals having at least one property that differs from one another; providing the plurality of power modulation signals to one or more power circuits; and driving the one or more light sources using one or more control signals generated by the one or more power circuits, wherein the one or more control signals are based on at least the plurality of power modulation signals.

In any of these examples, the at least one property is a frequency, a phase shift, a delay, a duty cycle, or a power.

In any of these examples, the at least one property varies across modulation periods.

In any of these examples, the one or more input frequencies are generated randomly or pseudo randomly.

In any of these examples, a frequency, a phase shift, or a duty cycle of the plurality of power modulation signals is the same across modulation periods.

In any of these examples, a frequency, a phase shift, or a duty cycle of the plurality of power modulation signals varies across modulation periods.

In any of these examples, the driving the one or more light sources comprises driving the same power during ON times of at least two modulation periods.

In any of these examples, the driving the one or more light sources comprises driving different powers during ON times of at least two modulation periods.

In any of these examples, the method further comprises: adjusting an intensity of light emanating from the one or more light sources, the adjusting comprising changing a duty cycle of the plurality of power modulation signals without changing the one or more input frequencies.

In any of these examples, the method further comprises: providing one or more linear signals to the one or more power circuits, wherein the one or more control signals are further based on the one or more linear signals.

In any of these examples, when an input to or an output from the one or more light sources is greater than or equal to a pre-determined level, an intensity of light emanating from the one or more light sources is controlled based on the one or more linear signals, and when the input to or the output from the one or more light sources is less than the pre-determined level, the intensity of the light emanating from the one or more light sources is controlled based on the one or more power modulation signals.

In any of these examples, the plurality of oscillators comprises at least one spread spectrum oscillator.

According to some examples, a system comprises: one or more light sources; a plurality of oscillators that generates a plurality of input signals based on one or more input frequencies; a controller that generates a plurality of power modulation signals based on the plurality of input signals, the plurality of power modulation signals having at least one property that differs from one another; and one or more power circuits that receive the plurality of power modulation signals and generate one or more control signals to drive the one or more light sources, wherein the one or more control signals are based on at least the plurality of power modulation signals.

In any of these examples, the system further comprises: one or more optical components, wherein during at least one modulation period, the one or more optical components operate at a frequency different from the frequency of the one or more power modulation signals.

In any of these examples, the one or more optical components comprise at least one of: a video camera, a pulse oximeter, an optical navigation system, or a location sensor.

In any of these examples, the at least one property is a frequency, a phase shift, a delay, a duty cycle, or a power.

In any of these examples, the at least one property varies across modulation periods.

In any of these examples, the one or more input frequencies are generated randomly or pseudo randomly.

In any of these examples, a frequency, a phase shift, or a duty cycle of the plurality of power modulation signals is the same across modulation periods.

In any of these examples, a frequency, a phase shift, or a duty cycle of the plurality of power modulation signals varies across modulation periods.

In any of these examples, the one or more power circuits drive the one or more light sources using the same power during ON times of at least two modulation periods.

In any of these examples, the one or more power circuits drive the one or more light sources using different powers during ON times of at least two modulation periods.

In any of these examples, the one or more power circuits further receives one or more linear signals, and wherein the one or more control signals are further based on the one or more linear signals.

In any of these examples, when an input to or an output from the one or more light sources is greater than or equal to a pre-determined level, an intensity of light emanating from the one or more light sources is controlled based on the one or more linear signals, and when the input to or the output from the one or more light sources is less than the pre-determined level, the intensity of the light emanating from the one or more light sources is controlled based on the one or more power modulation signals.

According to some examples, a system for powering one or more light sources comprises one or more processors, memory, and one or more programs stored in the memory for execution by the one or more processors and including instructions for: providing one or more input frequencies to a plurality of oscillators, wherein the plurality of oscillators generates a plurality of input signals based on the one or more input frequencies; generating a plurality of power modulation signals based on the plurality of input signals, the plurality of power modulation signals having at least one property that differs from one another; providing the plurality of power modulation signals to one or more power circuits; and driving the one or more light sources using one or more control signals generated by the one or more power circuits, wherein the one or more control signals are based on at least the plurality of power modulation signals.

In any of these examples, the at least one property is a frequency, a phase shift, a delay, a duty cycle, or a power.

In any of these examples, the at least one property varies across modulation periods.

In any of these examples, the one or more input frequencies are generated randomly or pseudo randomly.

In any of these examples, a frequency, a phase shift, or a duty cycle of the plurality of power modulation signals is the same across modulation periods.

In any of these examples, a frequency, a phase shift, or a duty cycle of the plurality of power modulation signals varies across modulation periods.

In any of these examples, the driving the one or more light sources comprises driving the same power during ON times of at least two modulation periods.

In any of these examples, the driving the one or more light sources comprises driving different powers during ON times of at least two modulation periods.

In any of these examples, the one or more programs include further instructions for adjusting an intensity of light emanating from the one or more light sources, the adjusting comprising changing a duty cycle of the plurality of power modulation signals without changing the one or more input frequencies.

In any of these examples, the driving the one or more light sources comprises providing one or more linear signals to the one or more power circuits, wherein the one or more control signals are further based on the one or more linear signals.

In any of these examples, when an input to or an output from the one or more light sources is greater than or equal to a pre-determined level, an intensity of light emanating from the one or more light sources is controlled based on the one or more linear signals, and when the input to or the output from the one or more light sources is less than the pre-determined level, the intensity of the light emanating from the one or more light sources is controlled based on the one or more power modulation signals.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The invention will now be described, by way of example only, with reference to the accompanying drawings, in which:

FIGS. 2A-2B illustrate exemplary waveforms for driving one or more light sources using fixed frequency PWM.

FIG. 3A illustrates an exemplary waveform for driving one or more light sources based on one or more power modulation signals having a frequency that varies across modulation periods, according to some aspects.

FIG. 3B illustrates an exemplary waveform for driving one or more light sources based on one or more power modulation signals having a power that varies across at least two modulation periods, according to some aspects.

DETAILED DESCRIPTION

Figure 1:
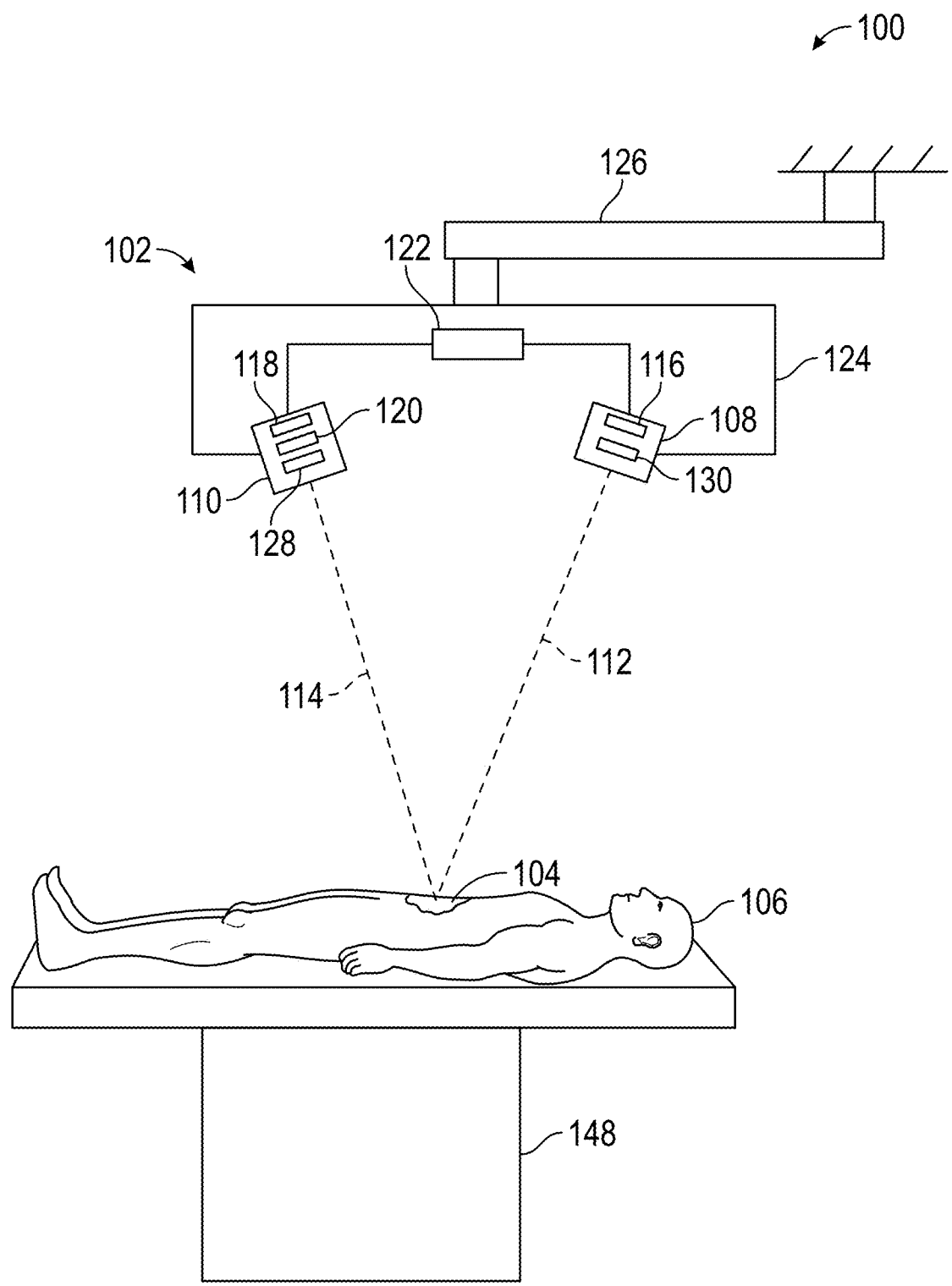
FIG. 1 illustrates a schematic representation of a lighting system, according to some aspects.

Reference will now be made in detail to implementations and various aspects and variations of systems and methods described herein. Although several exemplary variations of the systems and methods are described herein, other variations of the systems and methods may include aspects of the systems and methods described herein combined in any suitable manner having combinations of all or some of the aspects described.

Systems and methods according to the principles described herein can power one or more light sources to reduce interference between the light sources and/or optical components in the same environment. For example, the light sources may be surgical lights located in the same environment as a video camera. The light sources may be operated using one or more power modulation signals. The light sources and optical component(s) may be operating at the same time and with one or more properties (such as frequency) that are the same, which may cause optical and/or electrical interference. The interference may prevent the optical component(s) from operating properly.

The systems and methods described herein can automatically vary the frequency of the power modulation signals. This variation in frequency may reduce the optical interference at certain frequencies and/or spread the interference over multiple frequencies. This can reduce or avoid optical interference by reducing or avoiding operation of optical components (including the light sources of interest) at the same frequency at the same time.

According to various aspects, the frequency may be varied using an oscillator that generates an input signal (e.g., a clock signal) based on one or more input frequencies (e.g., clock frequencies). The light sources may receive one or more control signals, generated based on the varied frequency. The light sources may be driven in accordance with the frequency varying across modulation periods. Optionally, the frequency may be varied randomly or pseudo randomly.

The systems and methods described herein can introduce phase modulation into the control signals for driving channels of light sources to reduce the electrical interference. The system may introduce a difference in phase in the control signals to at least two channels, reducing or avoiding simultaneous or synchronous driving of the channels. The light sources may be driven using control signals having a respective phase shift. Optionally, a plurality (e.g., all) of the channels may be driven using control signals, each having unique phase shifts. The phase shift for a given channel may be equal to a certain degrees divided by the number of channels. In some aspects, the different phase shifts may lead to asynchronous driving of the plurality of channels.

The systems and methods described herein can vary one or more properties in the power modulation signals using a plurality of oscillators, one or more controllers, or a combination thereof. Exemplary properties may include, but are not limited to, frequency, phase shift, delay, duty cycle, and power.

The methods for powering one or more light sources, according to the principles described herein, can be used intraoperatively for guiding a surgeon during a surgical procedure. For example, the light sources may illuminate target tissue of a subject during a surgical procedure. The one or more light sources may be powered using the described systems and methods for non-surgical applications, such as for diagnosis or in support of non-surgical treatments.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general-purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates a schematic representation of a lighting system 100, according to some aspects. The lighting system 100 includes a surgical light 102 for illuminating target tissue 104 of a subject 106 with light from one or more light sources. The surgical light 102 includes a first light source 108 and a second light source 110. The first light source 108 emits first light 112 having a first spectrum for illuminating the tissue 104 with the first light 112. The second light source 110 emits second light 114 having a second spectrum for illuminating the tissue 104 with the second light 114.

A spectrum (e.g., first spectrum and/or second spectrum) may be a continuous spectrum that has wavelengths of light in a range from a lowest wavelength to a highest wavelength, or can be a discontinuous spectrum in which at least some wavelengths between the lowest and highest wavelengths of the light having the respective spectrum are not present in the light, such as a spectrum provided by a combination of red, green, and blue emitters. In some aspects, the light (e.g., first light 112 or second light 114) from a light source (e.g., first light source 108 or second light source 110) does not have light in a portion of the visible spectrum, or the light in the portion of the visible spectrum is attenuated with respect to the relative contribution of that portion of the visible spectrum to the light emitted from the respective light source. The first and second light sources 108 and 110 can be simultaneously activated so that the first light 112 and the second light 114 can combine, either at the target or prior to reaching the target, to illuminate the target tissue 104 with a mixture of the first light 112 and the second light 114. Thus, the tissue can be illuminated with light across a broad spectrum in which the relative contribution of light in the portion of the visible spectrum lacking from the second light 114 emitted by the second light source 110 is reduced with respect to the relative contribution of that portion of visible light relative to white light. In some aspects, reducing but not eliminating the relative amount of light in the portion of the visible spectrum lacking from the second light 114 of the second light source 110 (and thereby reducing but not eliminating the amount of that light that is reflected from the tissue) can preserve the normal appearance of the tissue while providing benefits to the user, such as improved contrast between features of the tissue, reduced fatigue, and/or reduced glare.

In some aspects, the first spectrum is broader than the second spectrum. For example, the first spectrum may be the visible spectrum. In some aspects, the first spectrum is narrower than the second spectrum but includes a portion of the visible spectrum lacking in the second spectrum. For example, the second spectrum may lack a given color, such as a red or blue, and the first spectrum may include just that color lacking from the second spectrum, such as the red or blue lacking from the second spectrum. According to various aspects, the first and/or second spectrums include non-visible light wavelengths, such as ultraviolet light and/or infrared light.

The lighting system 100 includes a controller 122 for controlling the first and second light sources 108 and 110. The controller 122 can be a component of the surgical light 102 as shown, or may be operatively coupled to the surgical light 102. The controller 122 controls the first and second light sources 108 and 110 such that the first and second light sources 108 and 110 emit the first and second lights 112 and 114, respectively, for providing the first and second spectrum lights to the tissue. In some aspects, the controller 122 can control the first and second light sources 108 and 110 according to different operating modes. For example, in a first mode, both light sources are activated to provide the first and second lights 112 and 114 to the target tissue 104, and in a second mode, the second light source 110 may be deactivated so that the target tissue is illuminated with only the first light 112. In some aspects, a third mode may be included in which the first light source 108 is deactivated and the second light source 110 is activated so that the tissue is illuminated with just the second light 114.

In some aspects, the surgical light 102 includes a housing 124 that houses the first and second light sources 108 and 110. In some aspects, the controller 122 is housed within the housing 124. The housing 124 may be mounted to a suspension arm assembly 126 so that the surgical light 102 can be suspended above subject 106, such as above an operating table 148 in an operating room. The suspension arm assembly 126 can attach to the ceiling or other suitable support.

The first light source 108 includes one or more first light emitters 116 that individually or collectively generate the first light 112. One or more optical elements 130 may be provided in front of the one or more light emitters 116 to manipulate the light emitted by the one or more light emitters for providing the light to the tissue of the subject 106, such as by focusing, collimating, collecting, homogenizing, and/or directing the light. The one or more optical elements 130 can include, for example, one or more lenses, mirrors, collimators, and filters.

The second light source 110 includes one or more second light emitters 118 that individually or collectively generate the second light 114. In some aspects, one or more filters 120 are provided to filter out a portion of the spectrum (entirely or at least a portion) attenuated from the second light 114 emitted by the second light source 110. In these aspects, the light emitted by the one or more second light emitters 118 includes light in the portion of the spectrum attenuated from the second light 114 emitted by the second light source 110, and the one or more filters 120 filter this light out so that the filtered portion of the spectrum is attenuated from the second light 114 provided by the second light source 110. In some aspects, the second light source 110 includes one or more optical elements 128 for manipulating light from the one or more second light emitters 118 for providing the light to the tissue of the subject. The one or more filters 120 can be located in any suitable location along the light path from the one or more second light emitters 118, including between the one or more second light emitters 118 and the one or more optical elements 128, downstream of the one or more optical elements 128, and/or directly on one or more surfaces of the one or more optical elements 128.

The light emitters of one or more of the first and second light sources 108 and 110, according to various aspects, can include any type of light emitter, such as incandescent (halogen lamp or a tungsten filament), discharge lamp, solid state, laser, or fluorescent light emitters. In some aspects, emitters of the first and second light sources 108 and 110 include one or more types of solid state light emitters such as one or more types of light-emitting diodes (LEDs), organic light-emitting diodes (OLED), superluminescent diodes (SLD), or polymer light-emitting diodes (PLED). In some aspects, light emitters of the first and second light sources 108 and 110 include narrow spectrum light emitters, such as red, green, and blue LEDs. In some aspects, light emitters of the first and second light sources 108 and 110 include broad spectrum light emitters, such as white light LEDs. In some aspects, the first and second light sources 108 and 110 have the same type or types of emitters. Alternatively, the first and second light sources 108 and 110 may have different types of emitters. In some aspects, the first and second light sources 108 and 110 can include phosphores. For example, in some aspects, the first and second light sources 108 and 110 may include emitters with different phosphores. In some aspects, the first and second light sources 108 and 110 both use at least one type of white light LED.

FIGS. 2A-2B illustrate exemplary waveforms for driving one or more light sources using fixed frequency PWM. The frequency 210 may be the same for each modulation period (e.g., periods P1, P2, P3, P4, P5, etc.). To adjust the intensity with fixed frequency PWM signals, the duty cycle may be adjusted. For example, the first waveform 220 of FIG. 2A may have a first duty cycle and a first ON time 222, and the second waveform 230 of FIG. 2B may have a second duty cycle and a second ON time 232. The second duty cycle (and second ON time 232) may be greater than the first duty cycle (and first ON time 222). As a result, the second waveform 230 may result in higher intensity than the first waveform 220.

The environment may be equipped with one or more optical components other than the light source(s). For example, the environment may be equipped with surgical lights and other optical components. Exemplary optical components may include, but are not limited to, video cameras, pulse oximeters, optical navigation systems, light bulbs, personal electronic devices, and location sensors. The other optical components may be operated at the same time as the light sources. In some instances, one or more of the other optical component(s)/system(s) may be operating at the same frequency as the frequency 210 of the light source(s), which may cause optical and/or electrical interference.

Although the frequency 210 may be changed such that the light source(s) no longer interfere with one or more optical components, the changed frequency may interfere with other optical components. The other optical components may operate at different frequencies. For example, a first optical component may operate at a first frequency, and a second optical component may operate at a second frequency. The light source(s) may operate at the first frequency, but then may be switched to a different frequency to avoid or reduce interference with the first optical component. The light source(s) may be switched to the second frequency, which may lead to interference with the second optical component. The light source(s) may be switched again to operate a different frequency, but given the number of optical components that may exist within the operating room, it may be difficult to reduce or avoid interference.

Examples of the disclosure may include reducing interference by varying the frequency of the power modulation signals. FIG. 3A illustrates an exemplary waveform 305 for driving one or more light sources based on one or more power modulation signals having a frequency that varies across modulation periods, according to some aspects. The frequency may differ for each modulation period. For example, the power modulation signal 305 may have a first frequency 310 for a first modulation period P1, a second frequency 312 for a second modulation period P2, a third frequency 314 for a third modulation period P3, etc.

The frequency of the power modulation signal(s) may vary continuously, as shown in the figure. This variation in frequency may reduce interference at certain frequencies and/or spread the interference over multiple frequencies. For example, depending on the frequencies of the other optical components in operation at the same time (in the same environment), the light sources may interfere with the other optical components at the first frequency 310, but not at the second frequency 312. As another example, depending on the frequencies of the other optical components in operation at the same time, the light source(s) may interfere with only a first optical component at the first frequency 310 and only a second optical component at the second frequency 312. In some aspects, a continuously varying frequency (of the power modulation signals) may have a frequency for the first modulation period P1 that is different from the frequency for the second modulation period P2, wherein the first modulation period P1 and the second modulation period P2 are consecutive periods.

In some aspects, the frequency of the power modulation signal(s) may vary randomly or pseudo randomly. That is, the frequency of the power modulation signal(s) may not be varied based on a pre-determined pattern. In some aspects, the frequency may vary for every modulation period. For example, as shown in the figure, the second frequency 312 for the second modulation period P2 may be different from the first frequency 310 for the first (adjacent) modulation period P1. The third frequency 314 for the third modulation period P3 may be different from the second frequency 312 for the second modulation period P2, etc. In some aspects, the third frequency 314 for the third modulation period P3 may be different from the first frequency 310 for the first modulation period P1.

In some examples, the duty cycle may vary across modulation periods. For example, during the first modulation period P1, the power modulation signals(s) 305 may have a first duty cycle 330. During the second modulation period P2, the power modulation signal(s) 305 may have a second duty cycle 332. During the third modulation period P3, the power modulation signal(s) 305 may have a third duty cycle 334. Alternatively, in some aspects, the duty cycle of the power modulation(s) may be the same across modulation periods. Additionally, in some aspects, the duty cycle of the power modulation(s) may differ across modulation signals. The duty cycle may be adjusted for finer granularity control of the illumination field, for example.

Examples of the disclosure may also include driving different powers or the same power during ON times of at least two of the modulation periods. FIG. 3B illustrates an exemplary waveform 355 for driving one or more light sources based on one or more power modulation signals having a power that varies across at least two modulation periods, according to some aspects. The driving may comprise driving different powers, such as power 340, power 342, and power 344, during ON times of at least two of the modulation periods, such as modulation period P1, modulation period P2, and modulation period P3, respectively. Additionally or alternatively, the driving may comprise driving the same power, such as power 346, during ON times of at least two of the modulation periods, such as modulation period P4 and modulation P5.

Figure 4A:
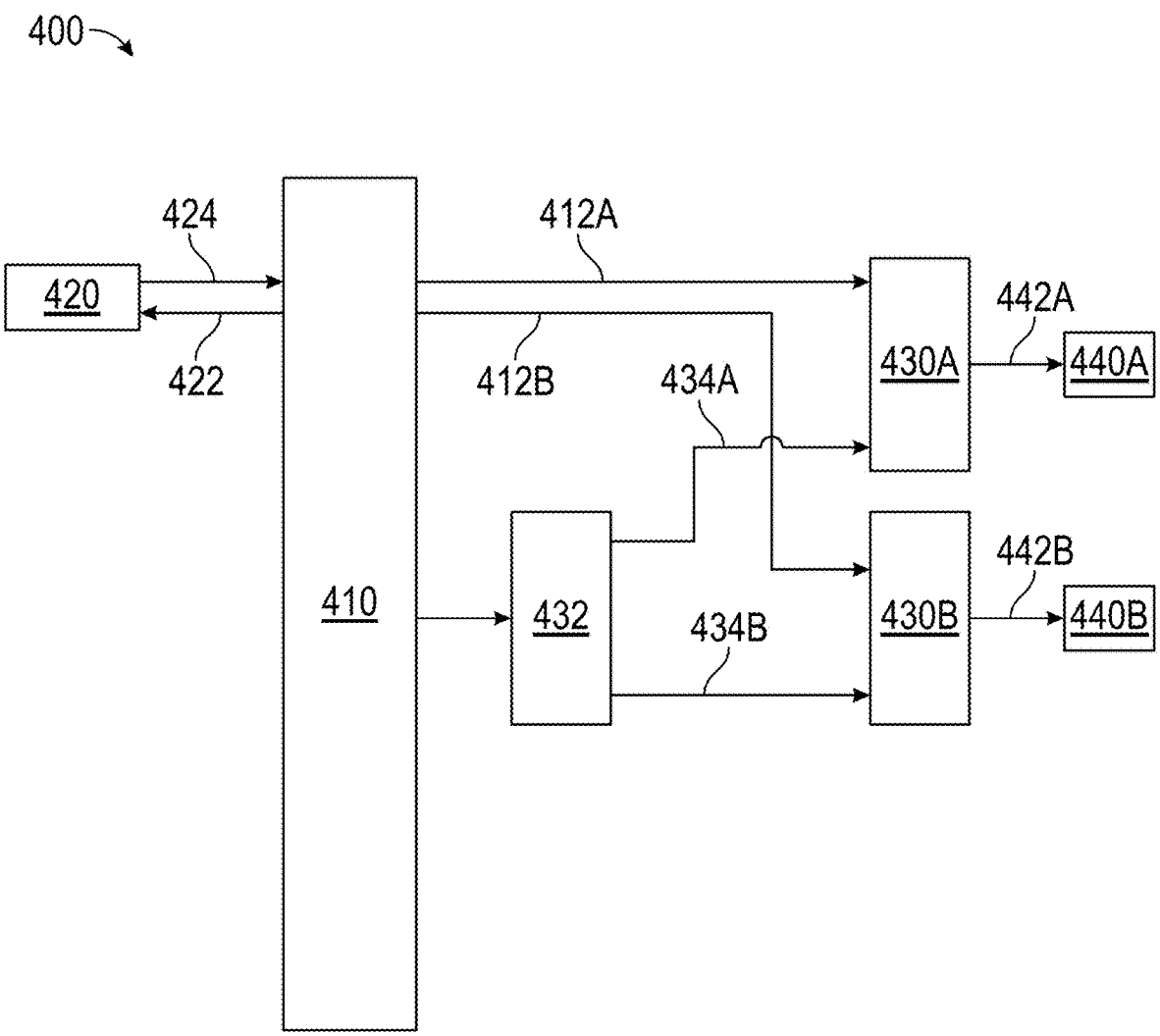
FIG. 4A illustrates an exemplary block diagram of a lighting system, according to some aspects.

FIG. 4A illustrates an exemplary block diagram of a lighting system, according to some aspects. The lighting system 400 may comprise one or more controllers 410, one or more oscillators 420, one or more power circuits 430, a converter 432, and one or more light sources 440. In some aspects, the controller(s) 410 may comprise one or more microcontrollers. In some aspects, the oscillator(s) 420 may comprise one or more spread spectrum oscillators. Although the figure illustrates controller(s) 410, oscillator(s) 420, power circuit(s) 430, and converter 432 as separate, discrete circuits, examples of the disclosure may include one or more circuits as included in another circuit. For example, oscillator 420 may be included in controller 410, converter 432 may be included in controller 410, etc.

The controller(s) 410 may include one or more programmable registers. The programmable registers may be set to select which component generates an input signal. Exemplary components for generating an input signal may include, but are not limited to, the controller(s) 410 and an external clock source (e.g., oscillator(s) 420). In some aspects, the controller 410 may provide the component (e.g., a spread spectrum oscillator) with one or more input frequencies (via signal 422), and the component may generate an input signal 424 based on the one or more input frequencies. The input signal and input frequencies may comprise, e.g., a clock signal and clock frequencies, respectively.

In some aspects, the controller(s) 410 may generate one or more power modulation signals 412 based on the input signal. The power modulation signals 412 may comprise at least a first power modulation signal 412A and a second power modulation signal 412B. The power modulation signal(s) may have a frequency that varies across modulation periods, as described throughout this disclosure. In some aspects, the frequencies may vary independently among a plurality of power modulation signals.

The controller(s) 410 may provide the power modulation(s) to the power circuit(s) 430. The converter 432 may receive a signal from the controller(s) 410 and may provide one or more linear signals 434 to the power circuit(s) 430. The linear signals 434 may comprise at least a first linear signal 434A and a second linear signal 434B. The power circuit(s) 430 may receive the power modulation signal(s) 412 and/or linear signal(s) 434 and may generate one or more control signals 442 to drive the one or more light sources 440. In some aspects, the control signal(s) 442 may be based on the power modulation signal(s) 412, linear signal(s) 434, or both. The light source(s) 440 may receive the control signal(s) 442 from the power circuit(s) 430 and emit light in response. In some aspects, each light source, such as light source 440A and 440B, may receive its own control signal from a unique power circuit, such as control signals 442A and 442B from power circuits 430A and 430B, respectively.

Examples of the disclosure may use one or more methods for controlling the intensity of the light emanating from one or more light sources. In some examples, the intensity may be controlled by using one or more linear signals. The one or more linear signals may be provided as control signals to drive the light source(s). The control signal may be, e.g., a current or voltage signal. Increased intensity may be achieved by driving a higher signal value (e.g., current), and decreased intensity may be achieved by driving a lower signal value. In some examples, the intensity may be controlled by using power modulation. Power modulation may comprise pulsing the light source(s), where the intensity may be controlled based on the proportion of ON time compare to OFF time of a given modulation period. Increased intensity may be achieved by driving a longer ON time, and decreased intensity may be achieved by driving a shorter ON time. Additionally or alternatively, the intensity of the light source(s) may be adjusted by changing the duty cycle of the power modulation signal(s). The duty cycle may be changed without changing the frequency (input to an oscillator, output from an oscillator, etc.).

In some aspects, different methods may be implemented for adjusting the intensity based on the input to or output from the light source(s). When one or more properties of the light source(s) meet a criterion, the intensity of the light source(s) may be controlled based on the linear signal(s). When the one or more properties of the light source(s) does not meet the criterion, the intensity of light source(s) may be controlled based on the power modulation signal(s). The criterion may be, as one non-limiting example, the input to or the output from the light source(s) being greater than or equal to a pre-determined level. As another non-limiting example, the criterion may be the light source(s) operating in a certain operating state. In this manner, any issues, such as those associated with color shifting and heating when operating the light source(s) at low intensity levels, may be reduced or avoided.

Examples of the disclosure include a comprising the lighting system 400 and one or more optical components located in the same environment (e.g., the same surgical room, medical facility, etc.). The optical component(s) may be located within the system or may be external from the system. Exemplary optical components may include, but are not limited to, a video camera, a pulse oximeter, an optical navigation system, and a location sensor.

Figure 4B:
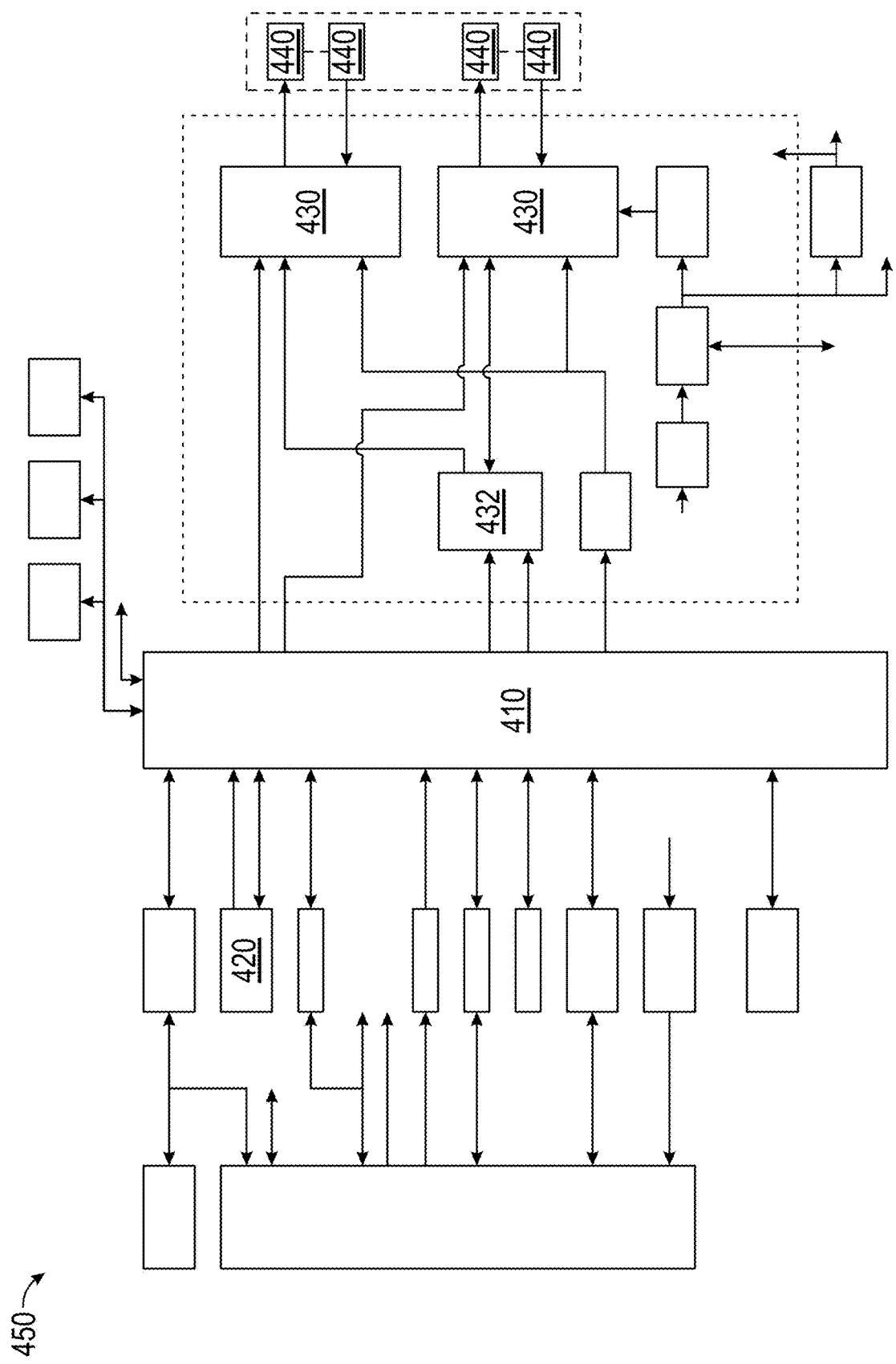
FIG. 4B illustrates an exemplary block diagram of a lighting system, according to some aspects.

FIG. 4B illustrates an exemplary block diagram of a lighting system, according to some aspects. The lighting system 450 may comprise the lighting system 400 of FIG. 4A including one or more controllers 410, one or more oscillators 420, one or more power circuits 430, one or more converters 432, and one or more light sources 440. The lighting system 450 may also comprise other components including, but not limited to, interface circuits, switches, drivers, inputs and outputs, protection circuits, sensors, memory, filters, and power supplies.

Figure 5:
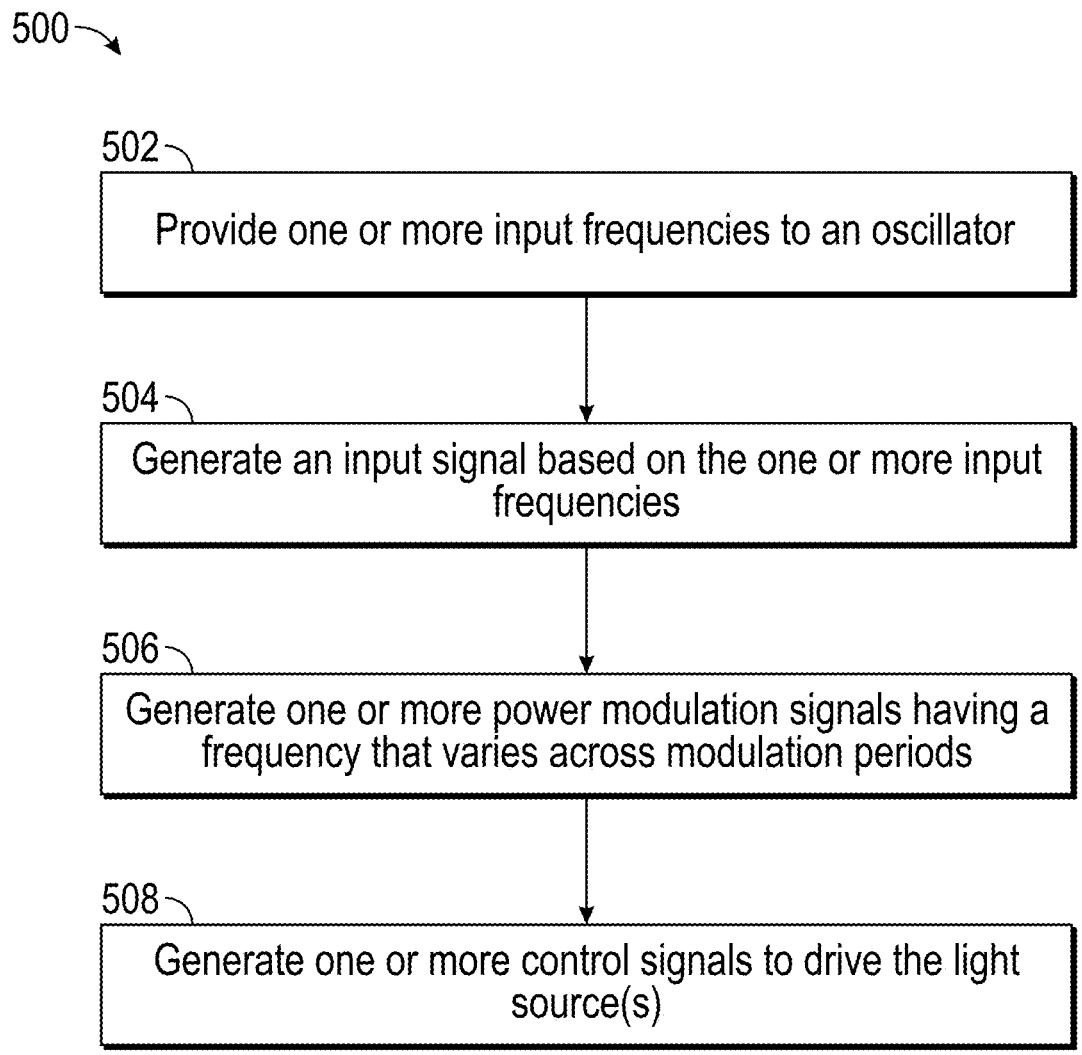
FIG. 5 illustrates a block diagram of an exemplary method for powering one or more light sources of the disclosed lighting system, according to some aspects.

FIG. 5 illustrates a block diagram of an exemplary method for powering one or more light sources of the disclosed lighting system, according to some aspects. The method 500 comprises a controller providing one or more input frequencies to an oscillator at step 502. At step 504, the oscillator may generate an input signal based on the one or more input frequencies. The controller may generate one or more power modulation signals based on the input signal at step 506, where the power modulation signal(s) may have a frequency that varies across modulation periods. At step 508, the one or more power circuits may receive the power modulation signal(s) and may generate one or more control signals to drive the light source(s).

During at least one modulation period, the frequency of at least one power modulation signal may be different from the frequency of at least another power modulation signal and/or the signal causing the operation of one or more optical components. The frequency of the power modulation signal(s) may vary across modulation periods. This difference (including the variation) in one or more frequencies may reduce or eliminate the amount of optical interference between the light sources in the lighting system and/or the optical component(s).

Figure 6:
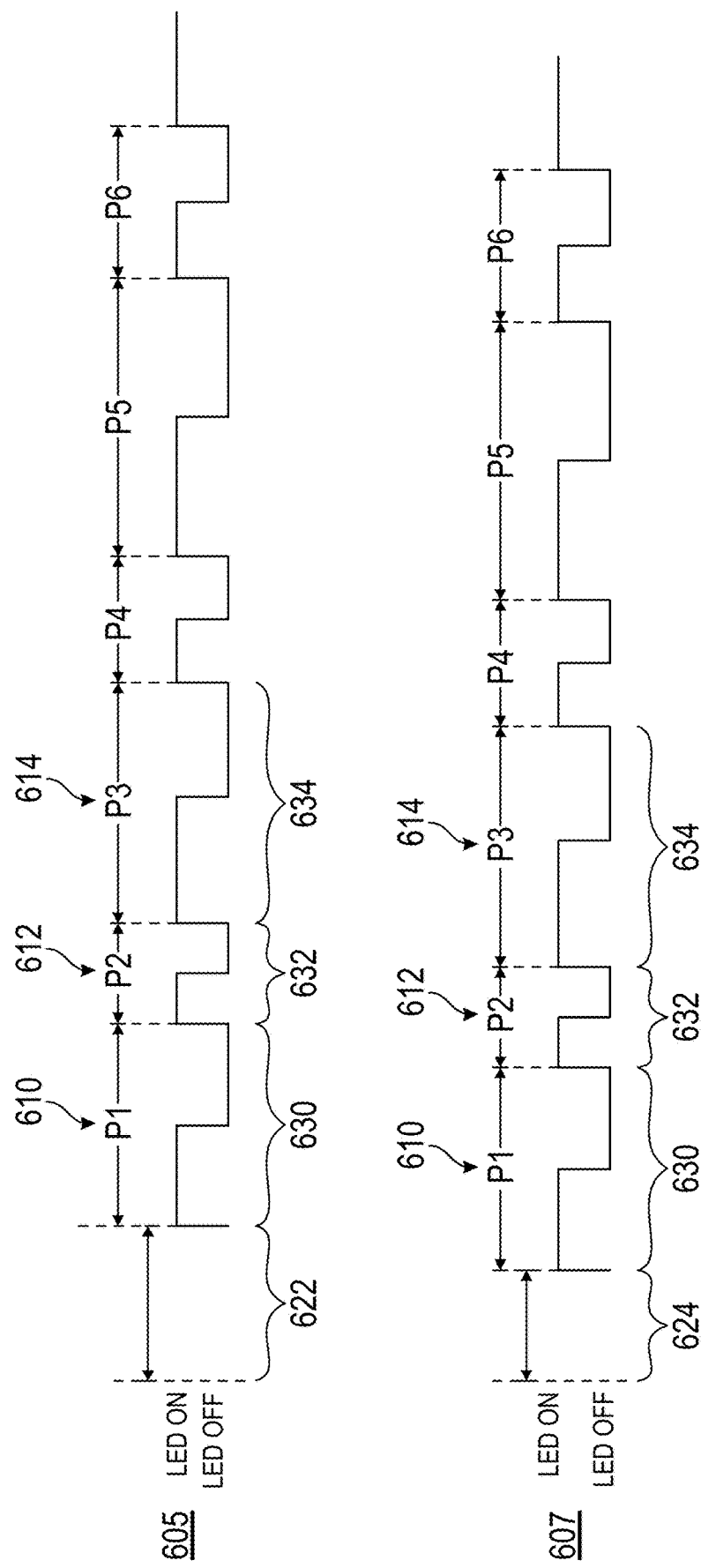
FIG. 6 illustrates exemplary waveforms for driving a plurality of channels having different phase shifts, according to some aspects.

Examples of the disclosure may include introducing phase modulation across channels to reduce electromagnetic interference (EMI). FIG. 6 illustrates exemplary waveforms 605 and 607 for driving a plurality of channels having different phase shifts, according to some aspects. The first power modulation signal 605 may have a first phase shift 622, and the second power modulation signal 607 may have a second phase shift 624. The first phase shift 622 (of the first power modulation signal 605) may be different from the second phase shift 624 (of the second power modulation signal 607) during the same modulation period.

The difference in phase shifts between the power modulation signals may reduce the combined interference from the channels. In some aspects, different channels may be driving different light source(s). For example, referring back to FIG. 4A, a first channel may be driving first light source(s) 440A and a second channel may be driving second light source(s) 440B. In some aspects, each channel may receive a unique set of control signals (including one or more power modulation signals 412 and/or one or more linear signals 434). Depending on the phase shift of the control signals of the light sources and/or other optical components in operation at the same time (in the same environment), the light sources may interfere with each other and/or with the other optical components.

Referring back to FIG. 6, in some aspects, the difference between the phase shift 622 of the first power modulation signal 605 and the phase shift 624 of the second power modulation signal 607 is the same over modulation periods, as shown in the figure. Alternatively, the difference between the phase shift 622 of the first power modulation signal 605 and the phase shift 624 of the second power modulation signal 607 may vary over modulation periods. This difference may vary randomly or pseudo randomly, for example. The phase shift of the power modulation signal(s) may not be varied based on a pre-determined pattern.

The difference between the phase shifts may be based on the number of power modulation signals, the number of channels, or both. As one non-limiting example, the phase shift for a given channel may be equal to a certain degrees divided by the number of channels, such as 36 degrees (360 degrees divided by 10 channels), 180 degrees (360 degrees divided by two channels), 90 degrees (360 degrees divided by four channels), etc. The phase shifts of the first, second, third, and fourth channels may be 0, 90, 180, and 270 degrees, respectively. In some aspects, the phase shift may reduce the power and noise by, e.g., the number of channels. For example, the power and noise may be reduced by a factor of four for four channels. The difference(s) between the phase shifts of two (or more) channels among the plurality of channels may be the same or different.

In some examples, the duty cycle may vary across modulation periods. For example, during the first modulation period P1, the power modulation signals(s) 605 may have a first duty cycle 630. During the second modulation period P2, the power modulation signal(s) 605 may have a second duty cycle 632. During the third modulation period P3, the power modulation signal(s) 605 may have a third duty cycle 634. Alternatively, in some aspects, the duty cycle of the power modulation(s) may be the same across modulation periods. The duty cycle(s) for the second waveform may follow the same pattern (first duty cycle 630, second duty cycle 632, third duty cycle 634, etc.) for multiple channels or may differ.

Examples of the disclosure may also include driving different powers or the same power during ON times of at least two of the modulation periods. Examples of the disclosure may, additionally or alternatively, use one or more methods for controlling the intensity of the light emanating from one or more light sources. In some examples, the intensity may be controlled by using one or more linear signals. The one or more linear signals may be provided as control signals to drive the light source(s). The control signal may be, e.g., a current or voltage signal. Additionally or alternatively, the intensity of the light emanating from the light source(s) may be adjusted by changing the duty cycle of the power modulation signal(s). The duty cycle of the power modulation signal(s) may be changed without changing other signals (input to an oscillator, output from an oscillator, etc.). In some aspects, different methods may be implemented for adjusting the intensity based on the input to or output from the light source(s). When the input to or the output from the light source(s) is greater than or equal to a pre-determined level, the intensity of the light emanating from the light source(s) may be controlled based on the linear signal(s). When the input to or the output from the light source(s) is less than the pre-determined level, the intensity may be controlled based on the power modulation signal(s).

The power modulation signals 605 and 607 of FIG. 6 may be generated from the lighting system shown in FIGS. 4A and 4B. The controller 410 may provide the component (e.g., an oscillator such as a spread spectrum oscillator) with one or more input frequencies (via signal 422), and the component may generate an input signal 424 based on the one or more input frequencies. The input signal 424 and input frequencies may comprise, e.g., a clock signal and clock frequencies, respectively.

The controller 410 may generate a plurality of power modulation signals 412 based on the input signal 424. The plurality of power modulation signals 412 may have different phase shifts relative to one another. For example, the first power modulation signal 412A may have a first phase shift, and the second power modulation signal 412B may have a second phase shift. The controller(s) 410 may provide the power modulation signal(s) 412 to the power circuits 430 and/or to the converter 432. The converter 432 may receive the signal from the controller(s) 410 and may provide one or more linear signals 434 to the power circuit(s) 430. The power circuit(s) 430 may receive the plurality of power modulation signals 412 and/or linear signal(s) 434 and may generate one or more control signals 442 to drive the one or more light sources 440.

In some aspects, the control signal(s) 442 may be based on the power modulation signal(s) 412, linear signal(s) 434, or both. The light source(s) 440 may receive the control signal(s) 442 from the power circuit(s) 430 and emit light in response. In some aspects, the first light source 440A may receive the first power modulation signal 412A, and the second light source 440B may receive the second power modulation signal 412B.

In some aspects, the lighting system 400 may be located in the same environment as one or more optical components (e.g., a video camera, a pulse oximeter, an optical navigation system, a location sensor, etc.). The one or more optical components may operate with a phase shift different from a phase shift of at least one of the plurality of power modulation signals.

Figure 7:
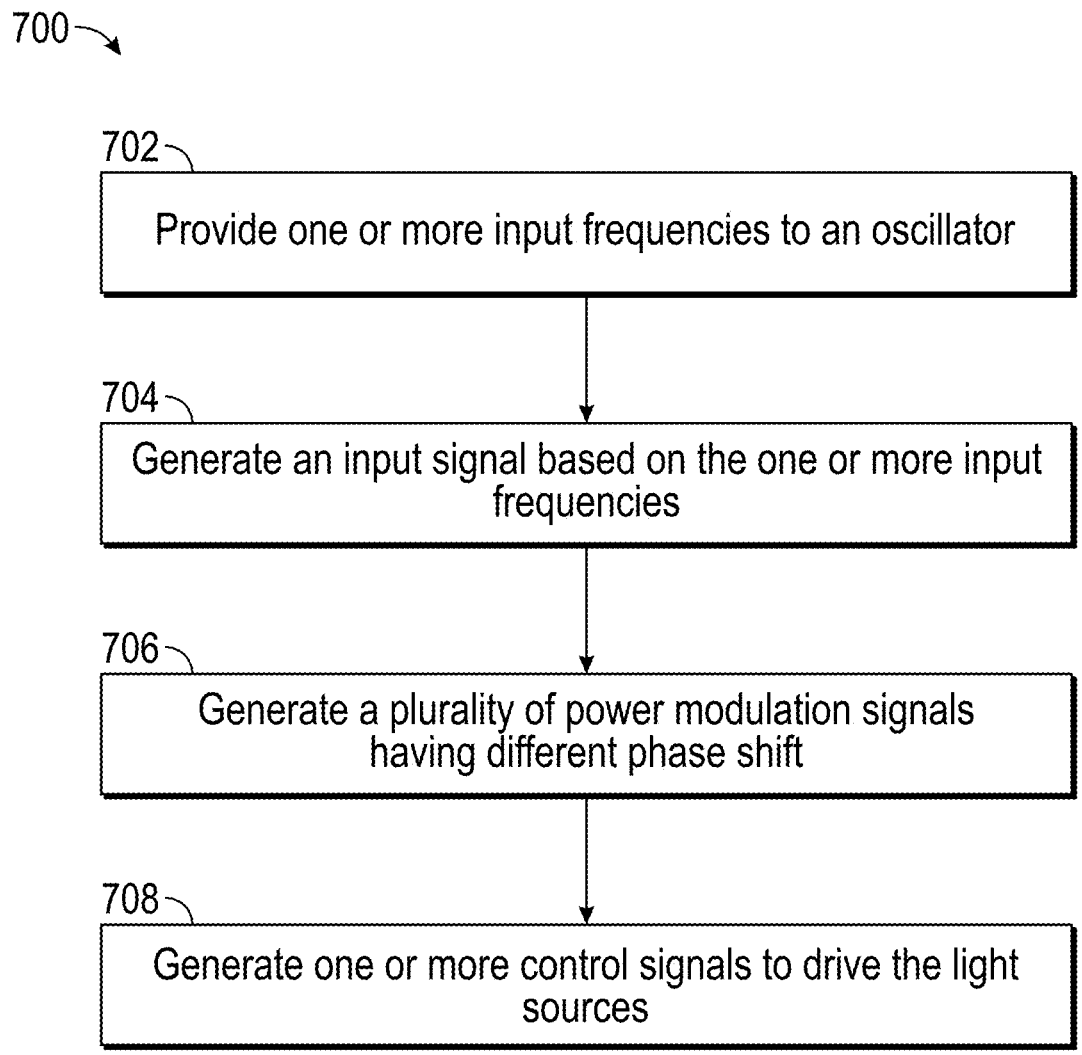
FIG. 7 illustrates a block diagram of an exemplary method for powering one or more light sources of the disclosed lighting system, according to some aspects.

FIG. 7 illustrates a block diagram of an exemplary method for powering one or more light sources of the disclosed lighting system, according to some aspects. The method 700 comprises a controller providing one or more input frequencies to an oscillator at step 702. At step 704, the oscillator may generate an input signal based on the input frequencies. The controller may generate a plurality of power modulation signals based on the input signal at step 706. Two or more of the generated plurality of power modulation signals may have different phase shifts. At step 708, the one or more power circuits may receive the plurality of power modulation signals and may generate one or more control signals to drive the light source(s).

During at least one modulation period, the phase shift of at least one of the plurality of power modulation signals may be different from the phase shift of another one of the plurality of power modulation signals and/or from a signal causing the operation of one or more optical components. The different phase shifts may be associated with different channels for driving one or more different light sources. This difference (including the variation) in one or more phase shifts may reduce or eliminate the amount of interference between the light sources in the lighting system and/or the optical component(s). In some aspects, the different phase shifts may lead to asynchronous driving of the plurality of channels.

Figure 8:
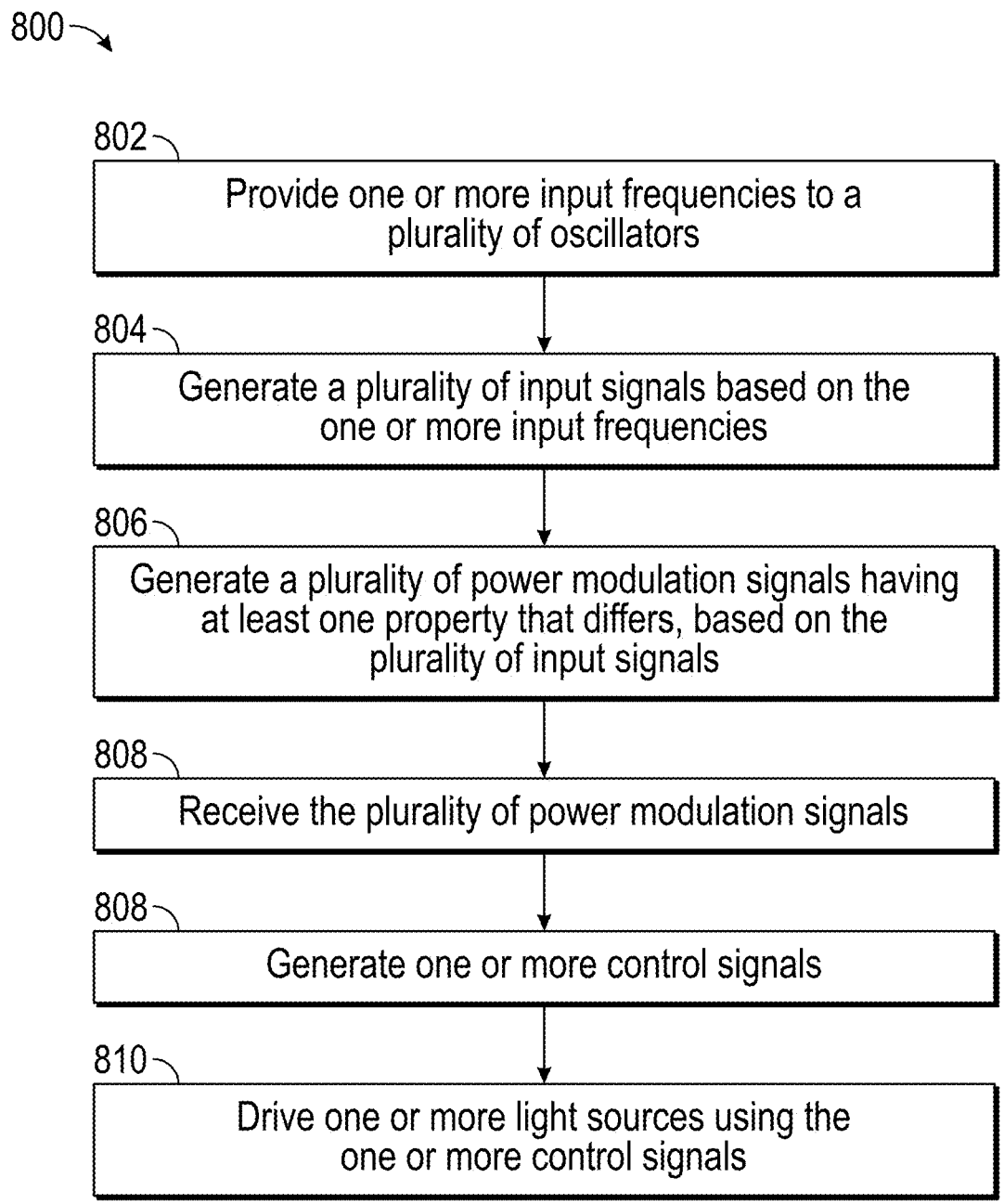
FIG. 8 illustrates a block diagram of an exemplary method for powering one or more light sources of the disclosed lighting system, according to some aspects.

Examples of the disclosure may comprise powering one or more light sources using a lighting system comprising a plurality of oscillators. The lighting system may be, e.g., light system 400 comprising a plurality of oscillators 420. FIG. 8 illustrates a block diagram of an exemplary method for powering one or more light sources of the disclosed lighting system, according to some aspects. The method 800 comprises a controller providing one or more input frequencies to a plurality of oscillators at step 802. The one or more input frequencies may be generated randomly or pseudo randomly. The plurality of oscillators may comprise at least one spread spectrum oscillator.

At step 804, the plurality of oscillators may generate a plurality of input signals based on the one or more input frequencies. The input signal may be a clock signal, and the one or more input frequencies may be clock frequencies, for example. At step 806, the controller may generate a plurality of power modulation signals, based on the plurality of input signals. In some aspects, the plurality of power modulation signals may have at least one property that differs from one another. For example, a first power modulation signal may have a first property, whereas a second power modulation signal may have a second property. Exemplary properties may include, but are not limited to, frequency, phase shift, delay, duty cycle, and power. The property may vary across modulation periods. The property (e.g., frequency, phase shift, or duty cycle) may vary or may be the same across modulation periods. In some aspects, the light source(s) may be driven using the same power during ON times of at least two modulation periods, or using different powers.

At step 808, the one or more power circuits may receive the plurality of power modulation signals. The power circuit(s) may generate one or more control signals (step 810) and may drive the one or more light sources using the one or more control signals (step 812). The one or more control signals may be based on at least the plurality of power modulation signals, at least one or more linear signals, or both.

In some aspects, a converter (e.g., converter 432) may provide one or more linear signals to the power circuits. The control signal(s) generated by the power circuit(s) may be further based on the linear signals. For example, when an input to or an output from (e.g., intensity level) the light source(s) is greater than or equal to a pre-determined level, the power circuit(s) may generate the control signal(s) based on the linear signal(s). Otherwise, the power circuit(s) may generate the control signal(s) based on the power modulation signal(s).

Figure 9:
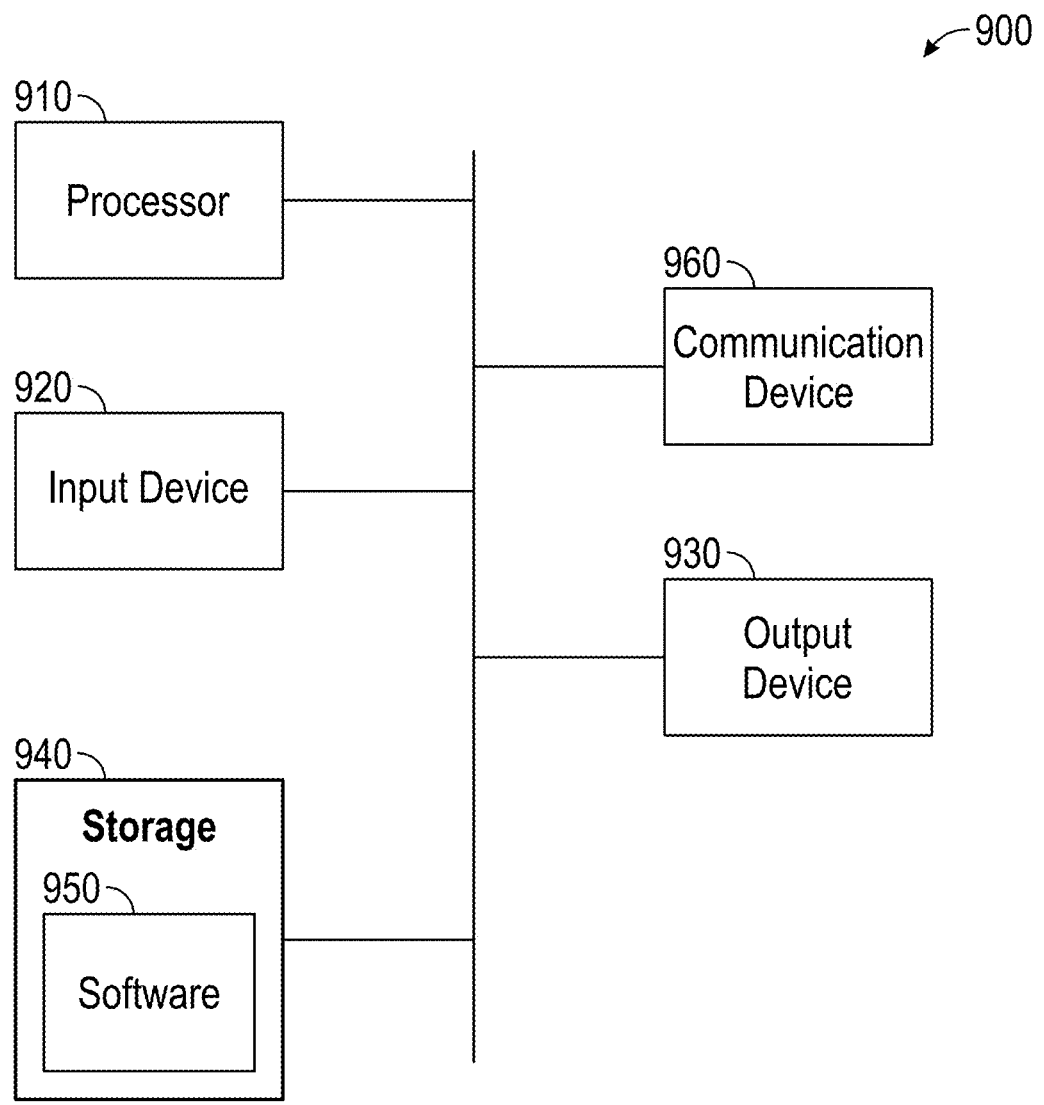
FIG. 9 illustrates an exemplary computing system, in accordance with some examples, that can be used for performing any of the methods and systems described herein, according to some aspects.

FIG. 9 illustrates an exemplary computing system, in accordance with some examples, that can be used for performing any of the methods described herein, including method 500 of FIG. 5, method 700 of FIG. 7, and method 800 of FIG. 8, and can be used for any of the systems described herein, including the lighting systems 400 and 450 of FIGS. 4A and 4B. System 900 can be a computer connected to a network, which can be, for example, an operating room network or a hospital network. System 900 can be a client computer or a server. As shown in FIG. 9, system 900 can be any suitable type of microcontroller or microprocessor-based system, such as an embedded control system, personal computer, workstation, server, or handheld computing device (portable electronic device) such as a phone or tablet. The system can include, for example, one or more of processors 910, input device 920, output device 930, storage 940, and communication device 960. Input device 920 and output device 930 can generally correspond to those described above and can either be connectable or integrated with the computer.

Input device 920 can be any suitable device that provides input, such as a touch screen, keyboard or keypad, mouse, gesture recognition component of a virtual/augmented reality system, or voice-recognition device. Output device 930 can be or include any suitable device that provides output, such as a touch screen, haptics device, virtual/augmented reality display, or speaker.

Storage 940 can be any suitable device that provides storage, such as an electrical, magnetic, or optical memory including a RAM, cache, hard drive, removable storage disk, or other non-transitory computer readable medium. Communication device 960 can include any suitable device capable of transmitting and receiving signals over a network, such as a network interface chip or device. The components of the computer can be connected in any suitable manner, such as via a physical bus or wirelessly.

Software 950, which can be stored in storage 940 and executed by processor 910, can include, for example, the programming that embodies the functionality of the present disclosure (e.g., as embodied in the devices as described above). For example, software 950 can include one or more programs for performing one or more of the steps of the methods disclosed herein.

Software 950 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 940, that can contain or store programming for use by or in connection with an instruction execution system, apparatus, or device.

Software 950 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic, or infrared wired or wireless propagation medium.

System 900 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 900 can implement any operating system suitable for operating on the network. Software 950 can be written in any suitable programming language, such as C, C++, C #, Java, or Python. In various examples, application software embodying the functionality of the present disclosure can be deployed in different configurations, such as in a client/server arrangement or through a Web browser as a Web-based application or Web service, for example.

The foregoing description, for the purpose of explanation, has been described with reference to specific aspects. However, the illustrative discussions above are not intended to be exhaustive or to limit the invention to the precise forms disclosed. Many modifications and variations are possible in view of the above teachings. The aspects were chosen and described in order to best explain the principles of the techniques and their practical applications. Others skilled in the art are thereby enabled to best utilize the techniques and various aspects with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method of powering one or more light sources, the method comprising:
   providing one or more input frequencies to a plurality of oscillators, wherein the plurality of oscillators generates a plurality of input signals based on the one or more input frequencies;
   generating a plurality of power modulation signals based on the plurality of input signals, the plurality of power modulation signals having at least one property that differs from one another;
   providing the plurality of power modulation signals to one or more power circuits;
   driving the one or more light sources using one or more control signals generated by the one or more power circuits, wherein the one or more control signals are based on at least the plurality of power modulation signals; and
   providing one or more linear signals to the one or more power circuits, wherein the one or more control signals are further based on the one or more linear signals;
   wherein:
      when an input to or an output from the one or more light sources is greater than or equal to a pre-determined level, an intensity of light emanating from the one or more light sources is controlled based on the one or more linear signals, and
      when the input to or the output from the one or more light sources is less than the pre-determined level, the intensity of the light emanating from the one or more light sources is controlled based on the one or more power modulation signals.

2. The method of claim 1, wherein the at least one property is a frequency, a phase shift, a delay, a duty cycle, or a power.

3. The method of claim 1, wherein the at least one property varies across modulation periods.

4. The method of claim 1, wherein the one or more input frequencies are generated randomly or pseudo randomly.

5. The method of claim 1, wherein a frequency, a phase shift, or a duty cycle of the plurality of power modulation signals is the same across modulation periods.

6. The method of claim 1, wherein a frequency, a phase shift, or a duty cycle of the plurality of power modulation signals varies across modulation periods.

7. The method of claim 1, wherein the driving the one or more light sources comprises driving the same power during ON times of at least two modulation periods.

8. The method of claim 1, wherein the driving the one or more light sources comprises driving different powers during ON times of at least two modulation periods.

9. The method of claim 1, further comprising:
   adjusting an intensity of light emanating from the one or more light sources, the adjusting comprising changing a duty cycle of the plurality of power modulation signals without changing the one or more input frequencies.

10. The method of claim 1, wherein the plurality of oscillators comprises at least one spread spectrum oscillator.

11. A system comprising:
    one or more light sources;
    a plurality of oscillators that generates a plurality of input signals based on one or more input frequencies;
    a controller that generates a plurality of power modulation signals based on the plurality of input signals, the plurality of power modulation signals having at least one property that differs from one another; and
    one or more power circuits that receive the plurality of power modulation signals and generate one or more control signals to drive the one or more light sources, wherein the one or more control signals are based on at least the plurality of power modulation signals, wherein the one or more power circuits further receives one or more linear signals, and the one or more control signals are further based on the one or more linear signals;
    wherein:
       when an input to or an output from the one or more light sources is greater than or equal to a pre-determined level, an intensity of light emanating from the one or more light sources is controlled based on the one or more linear signals, and
       when the input to or the output from the one or more light sources is less than the pre-determined level, the intensity of the light emanating from the one or more light sources is controlled based on the plurality of power modulation signals.

12. The system of claim 11, further comprising:
    one or more optical components, wherein during at least one modulation period, the one or more optical components operate at a frequency different from the frequency of the plurality of power modulation signals.

13. The system of claim 12, wherein the one or more optical components comprise at least one of: a video camera, a pulse oximeter, an optical navigation system, or a location sensor.

14. The system of claim 11, wherein the at least one property is a frequency, a phase shift, a delay, a duty cycle, or a power.

15. The system of claim 11, wherein the at least one property varies across modulation periods.

16. The system of claim 11, wherein the one or more input frequencies are generated randomly or pseudo randomly.

17. The system of claim 11, wherein a frequency, a phase shift, or a duty cycle of the plurality of power modulation signals is the same across modulation periods.

18. The system of claim 11, wherein a frequency, a phase shift, or a duty cycle of the plurality of power modulation signals varies across modulation periods.

19. The system of claim 11, wherein the one or more power circuits drive the one or more light sources using the same power during ON times of at least two modulation periods.

20. The system of claim 11, wherein the one or more power circuits drive the one or more light sources using different powers during ON times of at least two modulation periods.

21. A system for powering one or more light sources, the system comprising one or more processors, memory, and one or more programs stored in the memory for execution by the one or more processors and including instructions for:
    providing one or more input frequencies to a plurality of oscillators, wherein the plurality of oscillators generates a plurality of input signals based on the one or more input frequencies;
    generating a plurality of power modulation signals based on the plurality of input signals, the plurality of power modulation signals having at least one property that differs from one another;
    providing the plurality of power modulation signals to one or more power circuits; and driving the one or more light sources using one or more control signals generated by the one or more power circuits, wherein the one or more control signals are based on at least the plurality of power modulation signals, wherein the driving the one or more light sources comprises providing one or more linear signals to the one or more power circuits, wherein the one or more control signals are further based on the one or more linear signals;

wherein:
when an input to or an output from the one or more light sources is greater than or equal to a pre-determined level, an intensity of light emanating from the one or more light sources is controlled based on the one or more linear signals, and when the input to or the output from the one or more light sources is less than the pre-determined level, the intensity of the light emanating from the one or more light sources is controlled based on the one or more power modulation signals.

22. The system of claim 21, wherein the at least one property is a frequency, a phase shift, a delay, a duty cycle, or a power.

23. The system of claim 21, wherein the at least one property varies across modulation periods.

24. The system of claim 21, wherein the one or more input frequencies are generated randomly or pseudo randomly.

25. The system of claim 21, wherein a frequency, a phase shift, or a duty cycle of the plurality of power modulation signals is the same across modulation periods.

26. The system of claim 21, wherein a frequency, a phase shift, or a duty cycle of the plurality of power modulation signals varies across modulation periods.

27. The system of claim 21, wherein the driving the one or more light sources comprises driving the same power during ON times of at least two modulation periods.

28. The system of claim 21, wherein the driving the one or more light sources comprises driving different powers during ON times of at least two modulation periods.

29. The system of claim 21, wherein the one or more programs include further instructions for adjusting an intensity of light emanating from the one or more light sources, the adjusting comprising changing a duty cycle of the plurality of power modulation signals without changing the one or more input frequencies.

* * * * *